US011470791B2

United States Patent
Sellars et al.

(10) Patent No.: US 11,470,791 B2
(45) Date of Patent: Oct. 18, 2022

(54) SYSTEM AND METHOD FOR PROVIDING NUTRIENTS TO AN ALGAL GROWTH SYSTEM

(71) Applicant: Honda Motor Co., Ltd., Tokyo (JP)

(72) Inventors: Daniel T. Sellars, West Liberty, OH (US); Joel W. Agner, Bluffton, OH (US)

(73) Assignee: Honda Motor Co., Ltd., Tokyo (JP)

( * ) Notice: Subject to any disclaimer, the term of this patent is extended or adjusted under 35 U.S.C. 154(b) by 345 days.

(21) Appl. No.: 16/824,095

(22) Filed: Mar. 19, 2020

(65) Prior Publication Data
US 2021/0289727 A1 Sep. 23, 2021

(51) Int. Cl.
*A01G 33/00* (2006.01)
*C12M 1/00* (2006.01)
(Continued)

(52) U.S. Cl.
CPC .............. *A01G 33/00* (2013.01); *C05F 17/05* (2020.01); *C12M 23/02* (2013.01); *C12M 33/14* (2013.01);
(Continued)

(58) Field of Classification Search
CPC .. A01K 97/04; A01K 67/0332; A01K 67/033; A23K 1/188; A01N 3/00; A01G 33/00; C05F 17/05; C12M 23/02; C12M 23/22; C12M 21/02; C12M 33/14; C12N 1/12
See application file for complete search history.

(56) References Cited

U.S. PATENT DOCUMENTS 8,839,742 B2   9/2014  Bodlovich et al.
11,059,733 B2 * 7/2021  Tirman .................. C02F 3/327
(Continued)

FOREIGN PATENT DOCUMENTS

CN   102010110 A   4/2011
CN   102503018 A   6/2012
(Continued)

OTHER PUBLICATIONS

Espacenet Machine Translation of CN Patent No. 102010110 A.
(Continued)

*Primary Examiner* — Michael L Hobbs
(74) *Attorney, Agent, or Firm* — Plumsea Law Group, LLC (57) ABSTRACT

A system and method for converting food waste and other biologically-derived waste materials into nutrients for an algal growth system using worms to produce such nutrients is described. In one embodiment, a method for converting food waste into nutrients for an algal growth system using worms includes providing food waste to a container including a plurality of worms. The method also includes collecting castings from the food waste processed by the plurality of worms. The method further includes providing a wash to the container. The wash causes the castings to move to a bottom portion of the container adjacent to a moveable screen. The method includes actuating the moveable screen so that the castings pass through a plurality of holes in the moveable screen. The method also includes providing the passed castings to an algal growth system.

9 Claims, 5 Drawing Sheets

(51) Int. Cl.
  *C05F 17/05* (2020.01)
  *C12N 1/12* (2006.01)
  *C12M 1/26* (2006.01)

(52) U.S. Cl.
  CPC .............. *C12N 1/12* (2013.01); *C12M 21/02* (2013.01); *C12M 23/22* (2013.01); *Y02P 20/145* (2015.11); *Y02W 30/40* (2015.05)

(56) References Cited

U.S. PATENT DOCUMENTS

| | | | |
|---|---|---|---|
| 2012/0214223 A1* | 8/2012 | Hughes | C05F 17/05 119/6.5 |
| 2014/0137468 A1 | 5/2014 | Ching | |
| 2015/0196002 A1* | 7/2015 | Friesth | A01G 31/00 315/297 |
| 2016/0264484 A1 | 9/2016 | Guillard | |
| 2018/0116138 A1 | 5/2018 | Fung | |

FOREIGN PATENT DOCUMENTS

| | | |
|---|---|---|
| CN | 202265517 U | 6/2012 |
| CN | 103011909 A | 4/2013 |
| CN | 103461281 A | 12/2013 |
| CN | 102921710 B | 4/2015 |
| CN | 107624698 A | 1/2018 |
| CN | 207505745 U | 6/2018 |
| DE | 202014103397 U1 | 12/2015 |
| KR | 20130001836 U | 3/2013 |

OTHER PUBLICATIONS

Espacenet Machine Translation of CN Patent No. 102503018 A.
Espacenet Machine Translation of CN Patent No. 102921710 B.
Espacenet Machine Translation of CN Patent No. 103011909 A.
Espacenet Machine Translation of CN Patent No. 103461281 A.
Espacenet Machine Translation of CN Patent No. 107624698 A.
Espacenet Machine Translation of CN Patent No. 202265517 U.
Espacenet Machine Translation of CN Patent No. 207505745 U.
Espacenet Machine Translation of Published DE Patent Application No. 202014103397 U1.
Espacenet Machine Translation of Published KR Patent Application No. 20130001836 U.
Monisha Miriam, L.R., Edwin Raj, R., Kings, Ajith J., Adhi Visvanathan, M. (2016). Identification and characterization of a novel biodiesel producing halophilic Aphanothece halophytica and its growth and lipid optimization in various media. Energy Conservation and Management, 141 (2017), 93-100. <www.elsevier.com/locate/enconman>.

* cited by examiner

SYSTEM AND METHOD FOR PROVIDING NUTRIENTS TO AN ALGAL GROWTH SYSTEM

BACKGROUND

The present disclosure relates generally to composting, and more specifically to a system and method for converting food waste and other biologically-derived waste materials into nutrients for an algal growth system.

Currently, algae and other aquatic species are cultivated for the generation of useful materials and products, as well as the remediation of waste water, and carbon dioxide ($CO_2$) capture. Algal growth within a cultivation system is typically achieved or controlled by the use of synthetic nutrients designed to suit the end use of the generated biomass. These nutrients have significant cost associated with them, however, and make $CO_2$ capture, or generation of low value products such as fuel, not feasible.

There is a need in the art for a system and method that provides an improvement over the conventional techniques for algal growth cultivation.

SUMMARY

In one aspect, the disclosure provides a method for converting food waste into nutrients for an algal growth system using worms. The method includes providing food waste to a container including a plurality of worms. The method also includes collecting castings from the food waste processed by the plurality of worms. The method further includes providing a wash to the container. The wash causing the castings to move to a bottom portion of the container adjacent to a moveable screen. The method includes actuating the moveable screen so that the castings pass through a plurality of holes in the moveable screen. The method also includes providing the passed castings to an algal growth system.

In another aspect, the disclosure provides a system for converting food waste into nutrients for an algal growth system using worms. The system includes a container having a porous bottom. The container including a bedding material and a plurality of worms. The system also includes a moveable screen disposed adjacent to the porous bottom of the container. The moveable screen including a plurality of pores. The system further includes a waste stream for providing food waste to the container.

In still another aspect, the disclosure provides a system for converting food waste into nutrients for an algal growth system using worms. The system includes a waste stream at a location. The system also includes a nutrient reclamation system installed at the location of the waste stream. The system further includes an algal growth system located near the nutrient reclamation system. The nutrient reclamation system is configured to use worms to convert food waste from the waste stream into nutrients to be provided to the algal growth system.

Other systems, methods, features and advantages of the disclosure will be, or will become, apparent to one of ordinary skill in the art upon examination of the following figures and detailed description. It is intended that all such additional systems, methods, features and advantages be included within this description and this summary, be within the scope of the disclosure, and be protected by the following claims.

BRIEF DESCRIPTION OF THE DRAWINGS

The disclosure can be better understood with reference to the following drawings and description. The components in the figures are not necessarily to scale, emphasis instead being placed upon illustrating the principles of the disclosure. Moreover, in the figures, like reference numerals designate corresponding parts throughout the different views.

DETAILED DESCRIPTION

The techniques described herein provide systems and methods for converting food waste and other biologically-derived waste materials into nutrients for an algal growth system using worms to produce such nutrients.

Worms as well as other accelerated composting mechanisms, for example, microscopic organisms, such as bacteria and fungi, break down a multitude of complex compounds found within common industrial, municipal, and/or residential waste streams, including food waste. The compounds found in these waste streams are generally free (i.e., generated as a by-product), or a liability (i.e., requiring expenditures for proper disposal), and contain nutrients useful in the cultivation of algae. However, the nutrients contained in these waste streams are typically in a form that is not bio-available to the algae. In addition, the waste streams and nutrients may be contaminated with many useless and/or potentially harmful constituents, and therefore cannot be directly applied to an algal growth system.

As described herein according to the example embodiments, a wide variety of waste products can be broken down using worms and the valuable nutrients subsequently stored in a plant available form in the worm castings (i.e., excrement). The nutrients are water soluble, and, therefore, can be transferred to an algal growth system through steeping, percolation, or passing growth media through a filter bed of the worm castings.

Figure 1:
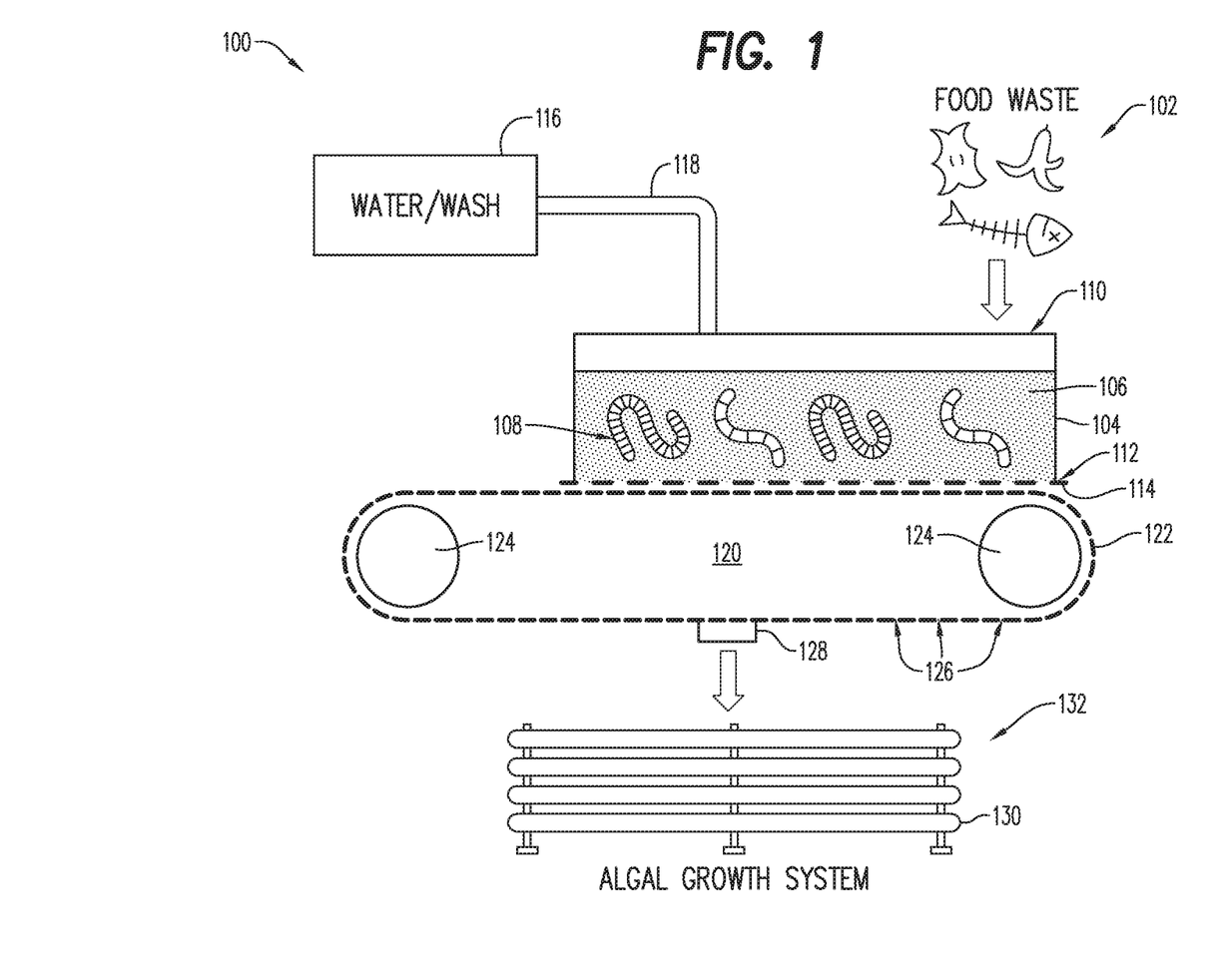
FIG. 1 is a schematic view of an example embodiment of a system for providing nutrients to an algal growth system.

Referring now to FIG. 1, an example embodiment of a nutrient reclamation system 100 for providing nutrients to an algal growth system 130 is shown. In some embodiments, nutrient reclamation system 100 (also referred to herein as "system 100") may be installed or located on-site near a source of waste, such as food waste 102. In this embodiment, system 100 includes a container 104 that is configured to hold and contain a bedding material 106, such as a combination of soil, compost, sand, organic matter, etc., in which a plurality of worms 108 are provided.

In one embodiment, worms 108 may be *Eisenia fetida* (commonly known as "Red Wigglers"). In other embodiments, worms 108 may be any suitable type or species of worms used for composting, including, but not limited to *Lumbricus rubellis, Eisenia andrei, Eisenia hortensis, Perionyx excavates, Dendrobaena veneta, Eudrilus eugeniae*, and others, including worms known by a variety of common names, including red worms, red wigglers, tiger worms, brandling worms, manure worms, and nightcrawlers. It should be understood that worms 108 may include a combination of different types or species. Additionally, the environment in which system 100 is installed or deployed may be better suited to one type or species of worms than others, based on temperature, humidity, and/or other environmental factors.

In an example embodiment, container 104 includes an opening at a top portion 110 to receive food waste 102 from a waste stream and a porous bottom portion 112. Container 104 including bedding material 106 and worms 108 serves as a reactor or vermicomposter in which food waste 102 is broken down. In some embodiments, container 104 may contain a filter media, or have holes or pores small enough at bottom portion 112 to retain solid materials. For example, in this embodiment, bottom portion 112 of container 104 includes a screen 114 having holes or pores that are sized so as to allow water or other liquid to pass through, but sufficiently large to retain the filter media and bedding material 106 inside container 104. In one embodiment, the pore size of screen 114 may be approximately 20 microns. In other embodiments, the pore size may be larger or smaller. For example, in some embodiments, the pore size may be from 20 microns to 100 microns. In other embodiments, the pore size may be greater than 100 microns.

In an example embodiment, food waste 102 from a waste stream is continually added to container 104 to support worms 108. Worms 108 eat or process food waste 102 and produce nutrient-rich castings (i.e., excrement). In this embodiment, system 100 also includes a water or wash source 116 that is in communication with container 104 via a tube 118 or other outlet mechanism. Using water/wash source 116, a liquid, such as water or the algal growth media from algal growth system 130, can be passed over bedding material 106 and the nutrient-rich castings contained within. The liquid (e.g., water or algal growth media) passes through container 104 and absorbs or dissolves the water soluble nutrients, such as nitrogen (N), phosphorus (P), and potassium (K), in the worm castings from bedding material 106. Solids are filtered out by the porous container bottom or filter media, for example, using screen 114, and the nutrient-rich liquid can be provided to algal growth system 130. For example, in some embodiments, a feed tube 128 or other mechanism may be used to funnel or channel the nutrient-rich liquid and/or castings to algal growth system 130.

In some embodiments, the holes or pores in screen 114 at bottom portion 112 of container 104 may be sized and dimensioned so as to allow the worm castings to pass through screen 114, but are large enough to retain bedding material 106 and other filter media inside container 104. For example, in one embodiment, the pore size of the holes or pores in screen 114 is approximately 20 microns. As noted above, in other embodiments, the pore size may be larger or smaller.

In an example embodiment, system 100 may include a harvesting mechanism 120 that includes a moveable screen 122 disposed beneath screen 114 of container 104. Moveable screen 122 includes a plurality of holes or pores 126. Plurality of holes or pores 126 of moveable screen 122 may be sized and dimensioned so as to allow the worm castings to pass through moveable screen 122, but are large enough to retain any bedding material 106 and other filter media that may be lost from container 104. For example, in one embodiment, the pore size of plurality of holes or pores 126 of moveable screen 122 is approximately 20 microns. In some embodiments, the pore size of moveable screen 122 may be substantially similar to the pore size of screen 114 of container. In other embodiments, the pore size of moveable screen may be larger or smaller than the pore size of screen 114. In addition, in various embodiments, the pore size may be larger or smaller.

Harvesting mechanism 120 includes a motor or other mechanism configured to turn rollers 124 that move moveable screen 122 to harvest the expelled worm castings that have accumulated along screen 114 of container 104. With this arrangement, moveable screen 122 scrapes or otherwise contacts the bottom of screen 114 to dislodge or remove the accumulated worm castings, thereby harvesting the castings for use in algal growth system 130. In an example embodiment, harvesting mechanism 120 may be in the form of an endless conveyor belt where moveable screen 122 moves in an endless loop configuration around rollers 124.

In addition, as shown in FIG. 1, feed tube 128 or other mechanism may be provided beneath container 104 and harvesting mechanism 120 to funnel or channel the nutrient-rich liquid and/or castings to algal growth system 130. With this arrangement, the nutrients contained in the castings that have been converted from food waste 102 by worms 108 may be supplied or provided to algal growth system 130 in a form that may be used by the algae for growth and reproduction.

In an example embodiment, algal growth system 130 includes a plurality of tubes 132 that are configured to hold the algae and water or other growth media. In some embodiments, plurality of tubes 132 may be glass or other transparent material that allows sunlight to pass through into the interior so that the algae contained within tubes may conduct photosynthesis. In the presence of sunlight, water, and the nutrients from system 100, the algae reproduce and grow. In different embodiments, algal growth system 130 may include many different species of algae. For example, most types of algae that are commercially grown in algae farms, such as algal growth system 130, are microalgae. These microalgae may also be referred to as phytoplankton, microphytes, and/or planktonic algae. However, in other embodiments, any suitable type of algae may be used in algal growth system 130.

Figure 2:
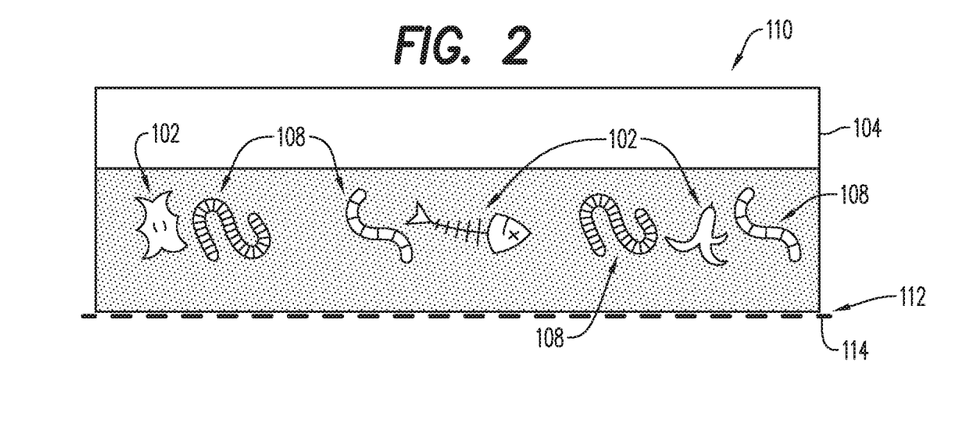
FIG. 2 is a representative view of an example embodiment of food waste being processed by worms.

Referring now to FIG. 2, an example embodiment of food waste 102 being processed by worms 108 is shown. In this embodiment, one or more items of food waste 102 have been provided to container 104 containing worms 108. For example, food waste 102 may be provided from a waste stream at the location where system 100 is installed or deployed. As shown in this embodiment, food waste 102 enters top portion 110 of container 104 containing bedding material 106 with plurality of worms 108. This food waste 102 provides food for worms 108, which eat food waste 102 and expel castings (i.e., excrement). In some embodiments, food waste 102 may be sorted to remove certain types or kinds of foods that are not optimal for composting. For example, many kinds of processed foods, meat scraps, and oily, salty, acidic, and/or spicy foods may be sorted out to remove them from food waste 102.

Figure 3:
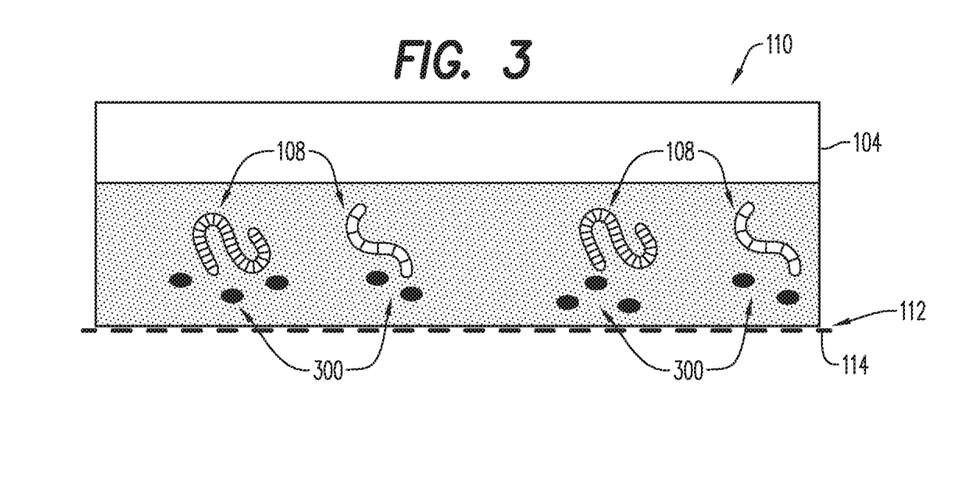
FIG. 3 is a representative view of an example embodiment of castings generated by worms after processing food waste.

FIG. 3 illustrates an example embodiment of worm castings 300 generated by worms 108 after processing food waste 108. In this embodiment, worms 108 have completely eaten or processed food waste 102 provided to container 104 from FIG. 2. As a by-product, worms 108 expel or generate castings 300. These castings 300 are intermingled with bedding material 106 in which worms 108 are living. As described above, castings 300 are rich in various nutrients derived from food waste 102, including, but not limited to nitrogen (N), phosphorus (P), and potassium (K).

Figure 4:
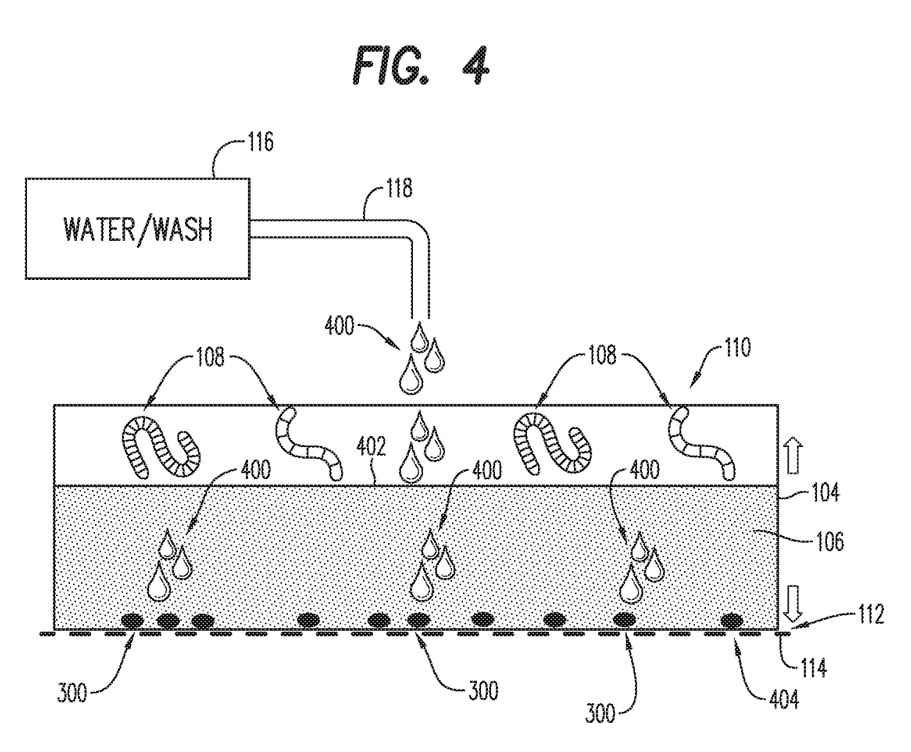
FIG. 4 is a representative view of an example embodiment of providing a wash to move castings towards a bottom of a container.

Referring now to FIG. 4, an example embodiment of providing a wash to move castings 300 towards bottom portion 112 of container 104 is shown. In some embodiments, water/wash source 116 may be provided to supply the wash to container 104. In some cases, the wash may be water. In other cases, the wash may be the algal growth media supplied or provided from algal growth system 130. For example, water/wash source 116 may obtain the algal growth media supplied via one of plurality of tubes 132 of algal growth system 130.

As shown in FIG. 4, water/wash source 116 provides wash 400 (e.g., water in this embodiment) to container 104 via tube 118 or other outlet mechanism. Tube 118 supplies wash 400 to container 104 at top portion 110. Wash 400 saturates bedding material 106. In response to wash 400, worms 108 surface at or near a top surface 402 of bedding material 106. That is, upon sensing the moisture in bedding material 106 from wash 400, worms 108 rise in a direction towards top portion 110 of container 104. Wash 400 causes worms 108 to be located along top surface 402 of bedding material 106 and to be absent from bottom portion 112 of container 104. With this arrangement, worms 108 are safely moved away from bottom portion 112 of container 104 so that they will not be harmed or injured during the harvesting of castings 300.

Additionally, wash 400 causes castings 300 to be dissolved in wash 400 and/or to move downward within bedding material 106 towards the porous screen 114 located at bottom portion 112 of container 104. That is, wash 400 causes castings 300 expelled by worms 108 to rest along screen 114 on bottom portion 112 of container 104 to expedite harvesting of castings 300 for use in algal growth system 130.

In this embodiment, screen 114 includes a plurality of holes or pores 404. Castings 300 and/or wash 400 including dissolved castings 300 are configured to pass through holes or pores 404 in screen 114 at bottom portion 112 of container 104. With this configuration, castings 300 and/or nutrient-rich wash 400 may pass through bedding material 106 to be harvested and supplied to algal growth system 130.

Figure 5:
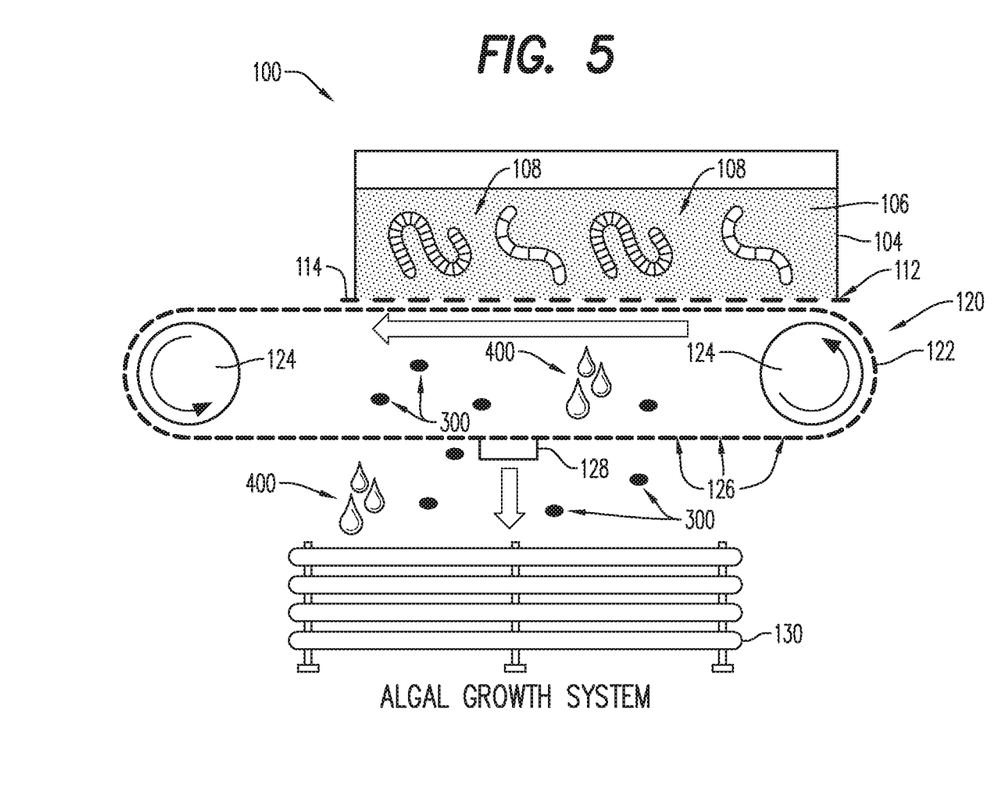
FIG. 5 is a schematic view of an example embodiment of a moveable screen for passing castings through to an algal growth system.

In some embodiments, a harvesting mechanism, for example, harvesting mechanism 120, described above, may be provided to assist or expedite harvesting castings 300 and/or nutrient-rich wash 400 from screen 114 along bottom portion 112 of container 102. Referring now to FIG. 5, an example embodiment of harvesting mechanism 120 including moveable screen 122 is shown for passing castings 300 through to algal growth system 130. As shown in this embodiment, moveable screen 122 is disposed beneath the porous bottom, for example, screen 114, of container 104. Harvesting mechanism 120 includes a motor or other mechanism configured to turn rollers 124 that move moveable screen 122 to harvest expelled worm castings 300 that have accumulated along screen 114 of container 104 after wash 400 has been provided to container 104.

For example, by action of rollers 124, moveable screen 122 scrapes or otherwise contacts the bottom of screen 114 to dislodge or remove the accumulated worm castings 300. The harvested castings 300, along with nutrient-rich wash 400 (i.e., water or other liquid provided from water/wash source 116 that has dissolved or absorbed water soluble nutrients contained in castings 300), pass through plurality of holes or pores 126 in moveable screen 122 to algal growth system 130. For example, in some embodiments, feed tube 128 or other mechanism may be used to funnel or channel nutrient-rich wash 400 and/or harvested castings 300 to algal growth system 130. With this arrangement, harvesting mechanism 120 may be provided to assist or expedite harvesting of castings 300 and/or nutrient-rich wash 400 for use in algal growth system 130.

Figure 6:
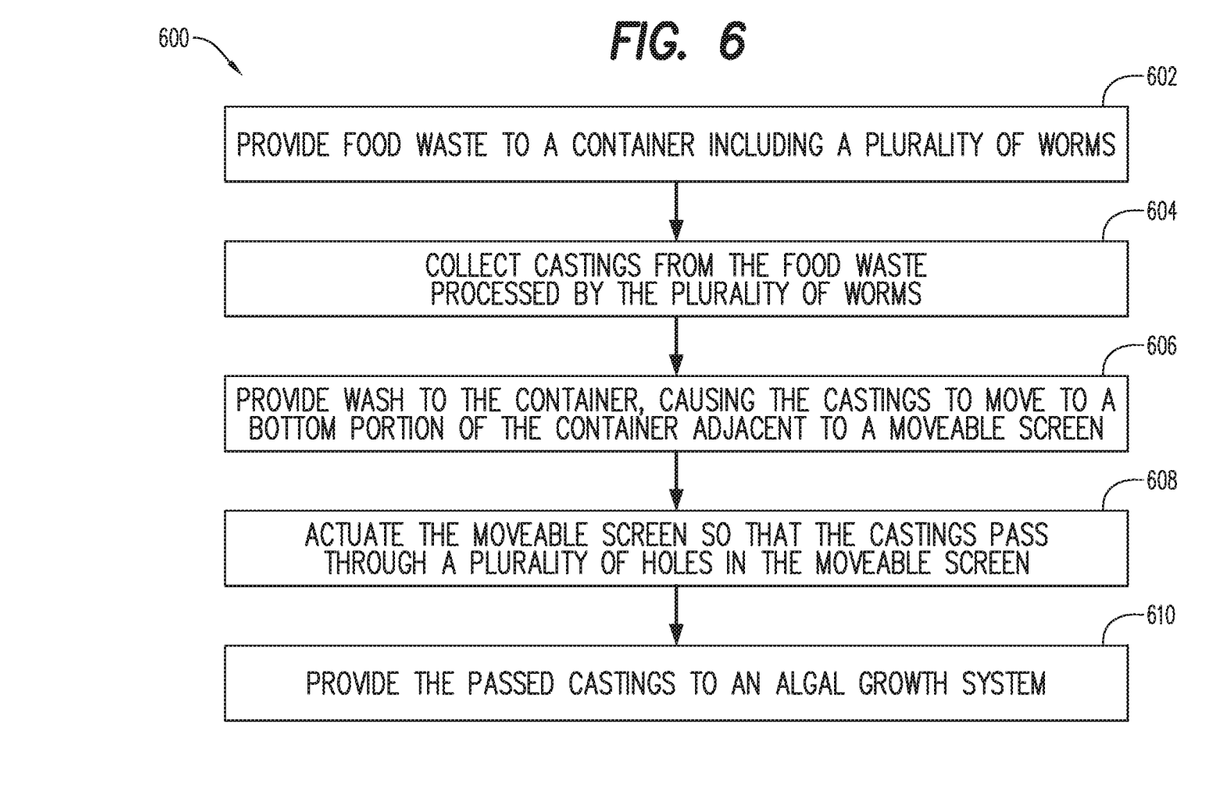
FIG. 6 is a flowchart of an example embodiment of a method for providing nutrients to an algal growth system.

Referring now to FIG. 6, an example embodiment of a method 600 for providing nutrients to an algal growth system is shown. In some embodiments, method 600 may be implemented using nutrient reclamation system 100 to provide nutrients to algal growth system 130. In this embodiment, method 600 begins with an operation 602. At operation 602, food waste is provided to a container including a plurality of worms. For example, at operation 602, food waste 102 may be provided from a waste stream to container 104 that includes plurality of worms 108 in bedding material 106.

Next, method 600 may proceed to an operation 604. At operation 604, castings from the food waste processed by the plurality of worms is collected. For example, at operation 604, castings 300 may be collected within bedding material 106 from food waste 102 eaten or processed by plurality of worms 108. In some embodiments, operation 604 of method 600 may be iterated multiple times or may last for a predetermined time period or duration so that an amount of castings is built up or collected within the bedding material for the worms (e.g., bedding material 106). Upon completion of operation 604 (i.e., once an amount of castings is collected), then method 600 may proceed to an operation 606.

At operation 606, a wash is provided to the container, causing the castings to move to a bottom of the container adjacent to a moveable screen. For example, as described above, wash 400 may be provided from water/wash source 116 via tube 118 into container 104 that includes bedding material 106 that has built up or collected an amount of castings 300 generated by worms 108 eating and processing food waste 102. Accordingly, at operation 606, wash 400 causes castings 300 to be dissolved in wash 400 and/or to move downward within bedding material 106 towards the porous screen 114 located at bottom portion 112 of container 104, as described above in reference to FIG. 4.

In some embodiments, method 600 may further include an operation 608. At operation 608, a moveable screen is actuated so that the castings pass through a plurality of holes or pores in the moveable screen. For example, as described above, harvesting mechanism 120 including moveable screen 122 having plurality of holes or pores 126 may be actuated via a motor to turn rollers 124 so that castings 300 disposed along bottom portion 112 of container 104 along screen 114 are scraped off by moveable screen 122. Additionally, actuation of the moveable screen may also assist with passing nutrient-rich wash liquid through from the container.

Next, method 600 includes an operation 610. At operation 610, the passed castings are provided to an algal growth system. For example, at operation 610, harvested castings 300 (i.e., harvested by actuation of moveable screen at operation 608) along with nutrient-rich wash 400 may pass through to algal growth system 130. Additionally, in some embodiments, feed tube 128 may be provided to funnel or channel castings 300 and/or nutrient-rich wash to algal growth system 130, for example, via one or more of plurality of tubes 132.

Method 600 may be implemented or iterated multiple times, including on demand and/or at a periodic or predetermined basis. For example, method 600 may be implemented upon expiration of a specific time period (e.g., once a week, once a day, etc.), upon providing a predetermined amount of food waste (e.g., after providing 100 pounds of food waste 102), upon determining a saturation level of castings within the worm's bedding material, or upon any other criteria or other factors. With this arrangement, method 600 may be used to extract nutrients from food waste using worms and provide the nutrients in a form that is bio-available to algae in an algal growth system.

While various embodiments of the disclosure have been described, the description is intended to be exemplary, rather than limiting and it will be apparent to those of ordinary skill in the art that many more embodiments and implementations are possible that are within the scope of the disclosure. Accordingly, the disclosure is not to be restricted except in light of the attached claims and their equivalents. Also, various modifications and changes may be made within the scope of the attached claims.

The invention claimed is:

1. A method for converting food waste into nutrients for an algal growth system using worms, the method comprising:
   providing food waste to a container including a plurality of worms;
   collecting castings from the food waste processed by the plurality of worms;
   providing a wash to the container, the wash causing the castings to move to a bottom portion of the container adjacent to a moveable screen;
   actuating the moveable screen so that the castings pass through a plurality of holes in the moveable screen; and
   providing the passed castings to an algal growth system.

2. The method according to claim 1, wherein collecting the castings includes collecting the castings for a predetermined amount of time.

3. The method according to claim 1, wherein collecting the castings includes collecting the castings associated with a predetermined amount of food waste.

4. The method according to claim 1, wherein providing the wash to the container includes providing water from a water source.

5. The method according to claim 1, wherein providing the wash to the container includes providing algal growth media from the algal growth system.

6. The method according to claim 1, wherein the container further includes a screen located at the bottom portion of the container adjacent to the moveable screen; and
   wherein actuating the moveable screen includes scraping the castings from the screen at the bottom portion of the container.

7. The method according to claim 1, wherein actuating the moveable screen includes using a harvesting mechanism including rollers to move the moveable screen.

8. The method according to claim 1, further comprising:
   using a feed tube located beneath the moveable screen to channel the passed castings to the algal growth system.

9. The method according to claim 1, wherein the plurality of holes in the moveable screen have a pore size of approximately 20 microns.

* * * * *